United States Patent
Griffiths (10) Patent No.: US 11,608,535 B2
(45) Date of Patent: Mar. 21, 2023

(54) DETECTION OF BACTERIAL INFECTIONS

(71) Applicant: The University of Liverpool, Liverpool (GB)

(72) Inventor: Michael Griffiths, Liverpool (GB)

( * ) Notice: Subject to any disclaimer, the term of this patent is extended or adjusted under 35 U.S.C. 154(b) by 0 days.

(21) Appl. No.: 17/046,268

(22) PCT Filed: Apr. 11, 2019

(86) PCT No.: PCT/GB2019/051048
§ 371 (c)(1),
(2) Date: Oct. 8, 2020

(87) PCT Pub. No.: WO2019/197833
PCT Pub. Date: Oct. 17, 2019

(65) Prior Publication Data
US 2021/0079483 A1    Mar. 18, 2021

(30) Foreign Application Priority Data

Apr. 12, 2018 (GB) .................................... 1806052

(51) Int. Cl.
C12Q 1/68       (2018.01)
C12Q 1/6888     (2018.01)
C12Q 1/689      (2018.01)

(52) U.S. Cl.
CPC ........... *C12Q 1/6888* (2013.01); *C12Q 1/689* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2004/0013663 A1 | 1/2004 | Choong-Chin et al. |
| 2004/0038201 A1* | 2/2004 | Nau .................... C12Q 1/6883 435/5 |
| 2009/0023149 A1 | 1/2009 | Knudsen |
| 2009/0291855 A1 | 11/2009 | Ryu et al. |
| 2010/0119474 A1 | 5/2010 | Crystal et al. |
| 2010/0216660 A1 | 8/2010 | Nikolsky et al. |
| 2015/0315643 A1 | 11/2015 | O'Garra et al. |
| 2016/0208331 A1 | 7/2016 | Storch |

FOREIGN PATENT DOCUMENTS

| | | | |
|---|---|---|---|
| FR | 2833968 A | 6/2003 | |
| WO | WO2015103664 A1 | 7/2015 | |
| WO | WO-2017068347 A1 * | 4/2017 | ........... C12Q 1/6883 |
| WO | WO2017068347 A1 | 4/2017 | |
| WO | 2017149548 A1 | 9/2017 | |
| WO | 2017214061 A1 | 12/2017 | |
| WO | WO-2017214061 A1 * | 12/2017 | ........... C12Q 1/6883 |
| WO | 2018011316 A1 | 1/2018 | |

OTHER PUBLICATIONS

Shebl. Cancer Epidemiol Biomarkers Prev. Apr. 2010 ; 19(4): 978-981. doi:10.1158/1055-9965.EPI-10-0064 (Year: 2010).*
Tang et al. Eur Resp J 2017; 49: 1602098, 12 pages (Year: 2017).*
Tortosa, et al., "Central nervous system gene expression changes in a transgenic mouse model for bovine spongiform encephalopathy," Veterinary Research, vol. 42, No. 109, 2011, 14 pages.
Tatebe, et al., Response network analysis of differential gene expression in human epithelial lung cells during avian influenza infections, BMC Bioinformatics, vol. 11, No. 170, 2010, 15 pages.
International Search Report and Written Opinion for PCT/GB2019/051048 dated Jul. 2, 2019, 12 pages.
Earls et al., Aurea: an open-source software system for accurate and user-friendly identification of relative expression molecular signatures, BMC Bioinformatics, Biomed Central, 2013, vol. 14(1).
Search Report issued in GB 1806052.5 dated Dec. 11, 2018, 4 pages.
Schwan, W.R., et al., "Detection and Characterization by Differential PCR of Host Eukaryotic Cell Genes Differentially Transcribed following Uptake of Intracellular Bacteria," Infection and Immunity, vol. 64, No. 1, Jan. 1996, pp. 91-99.

* cited by examiner

*Primary Examiner* — Juliet C Switzer
(74) *Attorney, Agent, or Firm* — Nixon Peabody LLP; Linda B. Huber (57) ABSTRACT

The present invention relates to methods of detecting an infection in a subject based on the relative abundance of target molecules indicative of the expression of at least the gene pair DUSP1 and IFI27. In particular, the invention relates to a method of distinguishing between a bacterial infection or a non-bacterial infection in a subject, especially between bacterial and non-bacterial lower respiratory system infections using the gene pair. Further, the invention provides the medical use of therapeutic agents in the treatment of a bacterial or non-bacterial infection in a subject identified as having such an infection through use of a method of the invention, and monitoring the therapeutic effectiveness.

13 Claims, 3 Drawing Sheets

DETECTION OF BACTERIAL INFECTIONS

CROSS-REFERENCE TO RELATED APPLICATIONS

This application is a National Phase of International Application No. PCT/GB2019/051048, filed Apr. 11, 2019, which designated the U.S. and that International Application was published under PCT Article 21(2) in English. This application also includes a claim of priority under 35 U.S.C. § 119(a) and § 365(b) to British patent application No. 1806052.5, filed Apr. 12, 2018, the entirety of which is hereby incorporated by reference in their entirety.

FIELD OF THE INVENTION

The present invention relates to methods of detecting an infection in a subject. In particular, the invention also relates to methods of detecting a bacterial infection and methods of detecting a non-bacterial infection in a subject. The present invention also relates to a method of distinguishing between a bacterial infection or a non-bacterial infection in a subject, especially between bacterial and non-bacterial lower respiratory system infection. Further, the invention provides the medical use of therapeutic agents in the treatment of a bacterial or non-bacterial infection in a subject identified as having such an infection through use of a method of the invention. The invention also relates to a method of treating an infection in a subject, and a method of detecting relative abundance of target molecules in a subject suspected of having or developing an infection.

INTRODUCTION

Infections, both bacterial and non-bacterial are a significant cause of morbidity and mortality in UK and worldwide. Infections can involve body compartments, organs or indeed the whole body. If left undiagnosed and untreated, infections can lead to sepsis, disability and sometimes loss of life.

Infections in some body compartments, such as the respiratory tract, can be difficult to diagnose because bacterial and viral infections, for example, present in the patient with the same symptoms.

Current methods of diagnosis for such infections are slow and laborious, typically involving samples being sent to a laboratory for testing with the results being provided after several days. For example, blood cultures often remain negative for a long time if the infection is caused by a slow growing bacteria. By this time, the infection may have spread considerably and have become unmanageable.

To combat this, patients are often given broad spectrum antibiotic treatment in case the infection is bacterial despite the lack of results confirming the presence of bacteria. This increases the cost of treatment that may not be effective and leads to the development of antibiotic resistance in the bacterial population.

It is an object of one or more of the aspects of the present invention to address the above-mentioned problems in the art.

SUMMARY OF THE INVENTION

In a first aspect, the invention relates to a method of detecting an infection in a subject, the method comprising:
(a) assaying a sample representative of gene expression in the subject to obtain data indicative of the relative abundance of target molecules indicative of the expression of at least the gene pair DUSP1 and IFI27;
(b) determining the presence of an infection in the subject in dependence on the data.

In a second aspect, the invention relates to method of detecting a bacterial infection in a subject, the method comprising:
(a) assaying a sample representative of gene expression in the subject to obtain data indicative of the relative abundance of target molecules indicative of the expression of at least the gene pair DUSP1 and IFI27;
(b) determining the presence of a bacterial infection in the subject in dependence on the data.

In a third aspect, the invention relates to a method of detecting a non-bacterial infection in a subject, the method comprising:
(a) assaying a sample representative of gene expression in the subject to obtain data indicative of the relative abundance of target molecules indicative of the expression of at least the gene pair DUSP1 and IFI27;
(b) determining the presence of a non-bacterial infection in the subject in dependence on the data.

In a fourth aspect, the invention relates to a method of distinguishing between a bacterial infection and a non-bacterial infection in a subject, the method comprising:
(a) assaying a sample representative of gene expression in the subject to obtain data indicative of the relative abundance of target molecules indicative of the expression of at least the gene pair DUSP1 and IFI27;
(b) determining the presence of a bacterial infection or non-bacterial infection in the subject in dependence on the data.

In a fifth aspect, the invention relates to a method of determining the cause of an infection in a subject, the method comprising:
(a) assaying a sample representative of gene expression in the subject to obtain data indicative of the relative abundance of target molecules indicative of the expression of at least the gene pair DUSP1 and IFI27;
(b) determining the cause of the infection as bacterial or non-bacterial in dependence on the data.

In a sixth aspect, the invention relates to an antibacterial agent for use in the treatment of a bacterial infection in a subject identified as having a bacterial infection by a method according to first, second, fourth and fifth aspect.

In a seventh aspect, the invention relates to a therapeutic agent for use in the treatment of a non-bacterial infection in a subject identified as having a non-bacterial infection by a method according to a first, third, fourth and fifth aspect.

A method of the first aspect, in which an infection is detected in a subject, may further comprise a step of providing the subject with treatment for the pathogen-associated infection.

Indeed, in an eighth aspect, the invention relates to a method of treating an infection in a subject, the method comprising:
(a) assaying a sample representative of gene expression in the subject to obtain data indicative of the relative abundance of target molecules indicative of the expression of at least the gene pair DUSP1 and IFI27;
(b) determining the presence of an infection in the subject in dependence on the data;
(c) providing treatment for an infection when the determination indicates the presence of an infection.

In a ninth aspect, the invention relates to a method of detecting the relative abundance of target molecules in a subject suspected of having or developing an infection, the method comprising:
(a) providing a sample representative of gene expression in the subject suspected of having or developing a pathogen-associated infection;
(b) detecting the relative abundance of target molecules indicative of the expression of at least the gene pair DUSP1 and IFI27.

In a tenth aspect, the invention relates to a method of monitoring the therapeutic effectiveness of a treatment for a subject having an infection, the method comprising:
(a) assaying a first sample representative of gene expression in the subject to obtain data indicative of the relative abundance of target molecules indicative of the expression of at least the gene pair DUSP1 and IFI27 in the first sample;
(b) providing the treatment to the subject;
(c) assaying a second sample representative of gene expression in the subject to obtain data indicative of the relative abundance of the same target molecules present in the second sample; and
(d) comparing the relative abundance of the target molecules in the first and second samples;
wherein a difference between the data indicative of the relative abundance of the target molecules in the first and second samples indicates the therapeutic effectiveness of the treatment.

A method of detecting an infection in a subject in accordance with the first aspect of the invention, or a method of detecting a bacterial infection in a subject in accordance with the second aspect of the invention, in which a bacterial infection is detected in a subject, may further comprise a step of conducting a further confirmatory test for the bacterial infection in the subject. Suitably, in such an embodiment, a bacterial infection is diagnosed when the results of both the first test (a method of the first and/or second aspect of the invention) and the second test (the confirmatory test) indicate the presence of bacterial infection. For example, a sample of biological fluid, such as CSF from lumbar puncture or blood from venepuncture, may be cultured in order to grow the microorganism associated with infection. This allows confirmation of bacterial infection and also allows determination of antimicrobial susceptibility of any isolated pathogen.

By the same token, a method of detecting a non-bacterial infection in a subject, in accordance with the third aspect of the invention, in which a non-bacterial infection is detected in a subject, may further comprise a step of conducting a further confirmatory test for the non-bacterial infection in the subject. Suitably, in such an embodiment, a non-bacterial infection is diagnosed when the results of both the first test (a method of the first and/or second aspect of the invention) and the second test (the confirmatory test) indicate the presence of non-bacterial infection. For example, a sample of biological fluid, such as a sputum or blood, may be tested for the presence of DNA from a non-bacterial pathogen (such as a virus or parasite). This allows confirmation of non-bacterial infection and also allows determination of appropriate treatment.

Methods in accordance with the first, second, third, fourth, fifth, eighth ninth, or tenth aspects of the invention may comprise obtaining data indicative of the relative abundance of target molecules indicative of the expression a further gene pair. Suitable examples of further gene pairs, and the benefits that may be gained by employing such further pairs, are described elsewhere in the present disclosure. Merely by way of example, further gene pairs particularly suitable for use in embodiments of the methods of invention may include at least one of: DUSP1 and SIGLEC1; ELANE and IFI27; DUSP1 and IFI44L; ELANE and SIGLEC1; or ELANE and IFI44L.

Unless required so by the context, references to the methods of the invention may be taken as encompassing the detecting methods of the first, second, third or ninth aspects of the invention, or methods of distinguishing between bacterial infection and non-bacterial infection of the fourth aspect, or method of determining the cause of infection according to the fifth aspect, or method of treating according to the eight aspect (and therefore the medical uses of the sixth or seventh aspects), or method of monitoring according to the tenth aspect.

DETAILED DESCRIPTION OF THE INVENTION

Infections, regardless of whether they are bacterial or non-bacterial, typically present with identical or very similar symptoms. This makes diagnosis and choice of a correct therapeutic approach difficult. In many cases, patients are given empirical antibiotic treatment, despite the lack of results confirming the presence of bacteria. This often leads to unnecessary treatment with antibiotics, which increases the cost of treatment and may lead to the development of antibiotic resistance.

The methods of the present invention provide simple tests that may be used for diagnosing infections, in particular for diagnosing and distinguishing between bacterial or non-bacterial infections. Such infections include, but are not limited to, lower respiratory tract infections, meningitis, and tropical diseases, for example malaria. Other examples of infections are discussed elsewhere in this specification.

Accordingly, the methods of the invention are advantageous, because they may allow a swifter identification of patients with suspected bacterial infections, which in turn, allows medical staff to commence appropriate treatment promptly, as well as prevent patients with non-bacterial infections from receiving unnecessary antibiotics. This advantageously reduces the problem of antibiotic resistance among pathogenic bacteria. Moreover, the inventors have surprisingly found that the methods of the invention diagnose and distinguish between bacterial and non-bacterial infections with a very high degree of sensitivity and specificity.

Furthermore, the methods of the present invention may allow the detection of bacterial infections, such as lower respiratory tract infections, even in cases where the sample is collected after the patients has already received antibiotics and/or other anti-microbial treatment. This is in contrast to conventional methods for detecting bacteria, such as bacterial culture, which often show poor sensitivity (fail to detect true cases of bacterial infection) when patient samples are collected after anti-microbial treatment has been initiated. Thus, the methods of the present invention may reduce the risk of missing true cases of bacterial infections among patients who have previously begun treatment with antibiotics.

In addition, the methods of the present invention can be used to detect infections remote from the source of the infection. The methods rely on the detection of the expression of one or more gene pairs that can be detected in any sample such as a blood sample, without requiring a sample to be taken from where the infection may be present. For example, a CNS infection may be detected from a blood sample rather than requiring a cerebrospinal fluid (CSF) sample to be taken.

The methods of the present invention are based on the inventors' selection of a specific gene pair, or combination of gene pairs, which allow(s) the detection of an infection, such as a bacterial or non-bacterial infection, as well as the distinction between a bacterial and non-bacterial infection.

The invention will now be described with reference to the following figures in which.

In order to assist the understanding of the present invention, certain terms used herein will now be further defined in the following paragraphs.

An infection

As used herein, the term "infection" refers the undesired presence and/or growth of a pathogen in a subject that has a negative effect on the subject's health and/or well-being. While the term "infection" should not be taken as encompassing the growth and/or presence of pathogens, such as bacteria, which are normally present in the subject (for example in the digestive tract of the subject), it may encompass the pathological overgrowth of such bacteria.

An infection may involve any body compartment. Accordingly, methods or medical uses of the present invention are applicable to infection in any system, organ or area of the subject, such as, but not limited to, lower respiratory system, upper respiratory system, central nervous system, gastrointestinal system, urinary system, the ocular system, the auditory system, and/or the skin.

Alternatively, the infection can also involve multiple body compartments, or in fact the whole body. Accordingly, methods and medical uses of the present invention are applicable to diseases such as bacteraemia, septicaemia, sepsis, Epstein-Barr virus infection, malaria, and helminthiasis.

Suitably, the infection is a pathogen-associated infection. In a suitable embodiment, the infection may be bacterial or non-bacterial. Such an embodiment gives rise to the second and third aspects of the invention.

Alternatively, the infection can be a combined bacterial and non-bacterial infection. For example, a bacterial infection may arise as a secondary infection due to a non-bacterial infection (such as a viral infection).

In a suitable embodiment, a non-bacterial infection is selected from the group consisting of a viral, a parasitic, a protozoan and a fungal infection. More suitably, a non-bacterial infection is a viral or a parasitic infection. Examples of bacterial or non-bacterial infections are discussed hereinbelow.

Bacterial Infection

A "bacterial infection" is an infection caused by the undesired presence and/or growth of bacteria in a subject.

In a suitable embodiment, bacterial infections may be caused by the growth and/or presence of gram positive and/or gram negative bacteria.

In a suitable embodiment, bacterial infections may be caused by the growth and/or presence of aerobic and/or anaerobic bacteria.

Merely by way of example, a bacterial infection may be caused by a bacterium selected from the group consisting of: *Acinetobacter baumannii, Actinomyces israelii, Bacillus anthracis, Bacillus cereus, Bacteroides fragilis, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila pneumoniae, Clostridium botulinum, Clostridium difficile, Clostridium perfringens, Clostridium tetani, Corynebacterium diphtheriae, Enterococcus faecalis, Enterococcus faecium, Escherichia coli, Ehrlichia canis, Ehrlichia chaffeensis, Haemophilus influenzae, Helicobacter pylori, Klebsiella pneumoniae, Legionella pneumonia, Leptospira interrogans, Leptospira santarosai, Leptospira weilii, Leptospira noguchii, Listeria monocytogenes, Moraxella catarrhalis, Mycoplasma pneumoniae, Neisseria gonorrhoeae, Neisseria meningitidis, Nocardia asteroids, Pseudomonas aeruginosa, Rickettsia rickettsia, Salmonella typhi, Salmonella typhimurium, Shigella sonnei, Shigella dysenteriae, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholera, Yersinia pestis, Yersinia enterocolitica*, and *Yersinia pseudotuberculosis*.

In one embodiment, the methods of the invention may be applied to bacterial infections caused by a bacterium selected from the group consisting of: *Streptococcus pneumoniae; Staphylococcus aureus, Pseudomonas aeruginosa, Klebsiella pneumoniae; Legionella pneumonia, Escherichia coli*, and *Haemophilus influenza.*

The inventors believe that the methods or medical uses of the invention according to the first, second, fourth, fifth, sixth eighth and tenth aspects are applicable to bacterial infections in which the bacterial pathogens are selected from any of the groups set out herein.

The methods and medical uses of the invention are believed to have utility in helping to diagnose bacterial infections of prosthetic implants. These may include implants in the head or other body compartments. Merely by way of suitable example the methods of the invention may be able to correctly distinguish bacterial infection from mechanical failure in ventriculo-peritoneal (VP) shunts, using either blood or CSF samples. It is anticipated the methods of the invention would work equally well using body fluid from other implants, such as CSF from external ventricular drains in the head, or synovial fluid from the joint space around prosthetic knee replacements.

Without detracting from the above, the methods and uses of the invention are particularly suitable for use in connection with bacterial infections in the lower respiratory tract, such as pneumonia as explained below.

Non-Bacterial Infection

A "non-bacterial infection" is an infection caused by the undesired presence and/or growth of a pathogen other than bacteria in a subject.

In a suitable embodiment, non-bacterial infections may be caused by the growth and/or presence of viruses, parasites, protozoa and/or fungi, for example.

In a suitable embodiment, the non-bacterial infections detected by methods of the invention may be caused by the growth and/or presence of viruses.

Merely by way of example, a non-bacterial infection may be caused by a pathogen selected from the group consisting of: influenza A, influenza B, human adenoviruses such as adenovirus 4 and 7, human respiroviruses, human rubulaviruses, human coronaviruses, Human orthopneumovirus, *Cryptosporidium parvum*, *Cryptosporidium hominis*, Human rhinoviruses, HIV, *Plasmodium falciparum*, herpes simplex virus, poliovirus, rabies virus, measles virus, west nile virus, arenavirus, reovirus, *Cryptococcus neoformans*, *Cryptococcus gatti*, *Histoplasma capsulatum*, Human metapneumovirus, Respiratory syncytial virus, Parainfluenza virus, Coxsackievirus, Echovirus, Coronavirus such as MERS-CoV or SARS, Hantavirus, Epstein-Barr virus, Cytomegalovirus, Human herpes virus 6, Varicella-zoster virus, and *Coccidioides immitis*.

In one embodiment, the methods of the invention may be applied to non-bacterial infections caused by viruses selected from: influenza A and influenza B.

The inventors believe that the methods or medical uses of the invention according to the first, third, fourth, fifth, seventh, eighth and tenth aspects are applicable to non-bacterial infections in which the pathogens are selected from any of the groups set out herein.

Lower Respiratory System Infection

The term "lower respiratory system infection" as used herein, refers to infection of a whole or part of the lower respiratory system caused by any form of pathogen. In a suitable embodiment, a lower respiratory system infection is an inflammation of the trachea, bronchi and/or lungs.

In one embodiment, the methods of the invention may be applied to lower respiratory system infections in a subject.

Lower respiratory system infections may include pneumonia, bronchitis, lung abscesses, bronchiolitis, tuberculosis, and flu, for example. Suitably, lower respiratory system infections are caused by a pathogen.

By way of example, bacteria typically associated with a lower respiratory system infection in human subjects may include: *Streptococcus pneumoniae, Haemophilus influenzae, Streptococcus pyogenes, Staphylococcus aureus, Klebsiella pneumoniae, Enterobacteria* (for example *Escherichia coli*), *Streptococcus agalactiae, Moraxella catarrhalis, Bordatella pertussis, Chlamydophila pneumoniae, Chlamydophila psittaci, Mycoplasma pneumoniae, Legionella pneumophila, Acinetobacter baumannii, Neisseria meningitidis, Coxiella burnetiid, Corynebacterium diphtheriae, Bordatella parapertussis, Neisseria gonorrhoeae, Campylobacter jejuni,* and *Listeria monocytogenes.*

By way of example, non-bacterial pathogens typically associated with lower respiratory system infection in human subjects may include: influenza A, influenza B, human adenoviruses, human respiroviruses, human rubulaviruses, human coronaviruses, Human orthopneumovirus, *Cryptosporidium parvum, Cryptosporidium hominis,* and Human rhinoviruses.

In some embodiments, the methods of the invention may be applied to bacterial lower respiratory system infections.

In some embodiments, the methods of the invention may be applied to non-bacterial lower respiratory system infections, such as viral lower respiratory system infections.

Suitably, the methods of the invention may be applied to a lower respiratory system infection caused by one or more of the following pathogens: *Streptococcus pneumoniae, Staphylococcus aureus, Streptococcus agalactiae, Streptococcus pyogenes, Pseudomonas aeruginosa, Bordatella pertussis, Neisseria meningitidis, Coxiella burnetiid, Corynebacterium, Klebsiella pneumoniae; Legionella pneumonia, Escherichia coli, Haemophilus influenza, Moraxella catarrhalis, Mycoplasma pneumoniae, Acinetobacter baumannii, Chlamydophila (Chlamydia) pneumoniae, Bordatella parapertussis, Neisseria gonorrhoeae, Campylobacter jejuni, Listeria monocytogenes,* Influenza virus A and B, Rhinovirus, Respiratory syncytial virus, Human metapneumovirus, Adenovirus 4 and 7, Respiroviruses, Rubulaviruses, Parainfluenza virus, Coxsackievirus, Echoviruses, Coronaviruses (MERS-Co V, SARS), Hantavirus, Orthopneumovirus, Epstein-Barr virus, Cytomegalovirus, Herpes simplex virus, Human herpesvirus 6, Varicella-zoster virus, Psittacosis (*Chlamydophila psittaci*), Q fever (*Coxiella bumetii*), Tularemia (*Francisella tularensis*), *Histoplasma capsulatum, Cryptococcus neoformans neoformans* and *Neoformans gattii, Coccidioides immitis, Cryptosporidium parvum, Cryptosporidium hominis, Mycobacteria tuberculosis* and nontuberculous mycobacteria.

Suitably, the methods of the invention may be applied to a lower respiratory system infection caused by one or more of the following bacterial pathogens: *Streptococcus pneumoniae, Haemophilus influenza, Staphylococcus aureus, Klebsiella pneumoniae, Escherichia coli, Pseudomonas aeruginosa, Legionella pneumonia, Moraxella catarrhalis, Mycoplasma pneumoniae, Chlamydophila psittaci, Coxiella bumetii, Francisella tularensis, Mycobacteria tuberculosis,* and *Chlamydophila (Chlamydia) pneumoniae.*

Suitably, the methods of the invention may be applied to a lower respiratory system infection caused by one or more of the following non-bacterial pathogens: Influenza virus A and B, Rhinovirus, Respiratory syncytial virus, *Histoplasma capsulatum,* Human metapneumovirus, *Cryptococcus neoformans, Cryptococcus gatti, Coccidioides immitis,* Adenovirus 4 and 7, Parainfluenza virus, Coxsackievirus, Echovirus, Coronavirus (MERS-Co V, SARS), Hantavirus, Epstein-Barr virus, Cytomegalovirus, Herpes simplex virus, Human herpesvirus 6 and Varicella-zoster virus.

In one embodiment, the methods of the invention may be applied to a lower respiratory system infection caused by one or more of the following pathogens: *Streptococcus pneumoniae; Staphylococcus aureus, Pseudomonas aeruginosa, Klebsiella pneumoniae; Legionella* pneumonia, *Escherichia coli, Haemophilus* influenza, and Influenza virus A and B.

As illustrated by the results presented in the examples section, the methods of the invention are able to distinguish between bacterial and non-bacterial lower respiratory system infections.

Suitably, particular pathogens may be associated with particular lower respiratory system infections.

Suitably, pneumonia may be caused by any of the following pathogens: *Chlamydia pneumoniae, Escherichia coli, Haemophilus influenza, Klebsiella pneumoniae, Legionella pneumonia, Moraxella catarrhalis, Mycoplasma pneumoniae, Neisseria meningitides, Pseudomonas aeruginosa, Staphylococcus aureus, Streptococcus agalactiae,* and *Streptococcus pneumoniae.*

In one embodiment, the methods of the invention may be applied to pneumonia in a subject. Suitably the pneumonia may be viral, bacterial, fungal or parasitic. In one embodiment, the methods of the invention may be applied to pneumonia caused by one or more of the following pathogens: *Chlamydia pneumoniae, Escherichia coli, Haemophilus influenza, Klebsiella pneumoniae, Legionella pneumonia, Moraxella catarrhalis, Mycoplasma pneumoniae, Neisseria meningitides, Pseudomonas aeruginosa, Staphylococcus aureus, Streptococcus agalactiae,* and *Streptococcus pneumoniae.*

Bacterial Infection Syndromes

The term "bacterial infection syndrome" as used herein, refers to conditions caused by, or resulting from, the presence of a bacterial infection in a subject. Such conditions may be systemic or isolated to a particular tissue or organ of the body.

Suitably a bacterial infection syndrome may be caused by a subject's response to a bacterial infection.

Suitably, a bacterial infection syndrome may be caused by or associated with inflammation and/or injury of tissue(s) or organ(s) due to a bacterial infection.

Suitably a bacterial infection syndrome may involve a particular tissue or organ, or may involve multiple tissues or organs.

Suitably a bacterial infection syndrome involving a particular tissue or organ may be selected from: pneumonia (inflammation of the lower respiratory tract), pyelonephritis, urinary tract infection, gastroenteritis, cellulitis, impetigo, meningitis and osteomyelitis.

Suitably a bacterial infection syndrome involving multiple tissues or organs may be selected from sepsis.

Accordingly, the methods of the invention may be applied to a bacterial infection syndrome.

In one embodiment, the methods of the invention may be applied to sepsis and/or bacterial gastroenteritis.

By way of example, bacteria typically associated with sepsis in human subjects may include: *Staphylococcus* species (e.g. *Staphylococcus aureus*), *Streptococcus pyogenes, Escherichia coli, Pseudomonas aeruginosa, Klebsiella* species, *Streptococcus pneumonia* and *Neisseria meningitidis.*

In one embodiment, the methods of the invention may be applied to sepsis caused by a bacterium including: *Staphylococcus* species (e.g. *Staphylococcus aureus*), *Streptococcus pyogenes, Escherichia coli, Pseudomonas aeruginosa, Klebsiella* species, *Streptococcus pneumonia* and *Neisseria meningitidis.*

By way of example, bacteria typically associated with gastroenteritis in human subjects may include: *Escherichia coli, Campylobacter jejuni, Salmonella enterica, Shigella dysenteriae.*

In one embodiment, the methods of the invention may be applied to bacterial gastroenteritis caused by a bacterium including: *Escherichia coli, Campylobacter jejuni, Salmonella enterica, Shigella dysenteriae.*

Detecting Infections

The methods of the first, second and third aspects of the invention are methods for detecting an infection, detecting a bacterial infection and detecting a non-bacterial infection, respectively. In the context of the present disclosure, the term "detecting" is taken as meaning determining the presence of an infection, in particular a bacterial and/or a non-bacterial infection in a subject.

Suitably, the methods of the invention may be used to detect lower respiratory system bacterial and/or non-bacterial infections, suitably which may be caused by any of the pathogens described in the relevant sections above. Suitably, the methods of the invention may be used to detect bacterial infection syndromes, suitably which may be caused by any of the pathogens described in the relevant section above.

In one embodiment, the method of the invention may be used to detect an infection that is associated with symptoms in a subject. Alternatively, the methods may also be used to detect an infection that is essentially asymptomatic. Such asymptomatic infections may be infections that are at a very early stage.

The inventors believe that the assessment, in the methods of the invention, of expression of genes associated with the subject's host response to bacterial infections to provide information regarding the presence of this condition confers notable advantages. Without wishing to be bound by any hypothesis, one such advantage may be that target molecules indicative of expression of such genes are found at detectable levels at earlier time points than are potential markers expressed by the bacteria associated with the infection. While levels of expression of bacterial genes may be difficult to detect, especially during the early stages of bacterial infections, the expression of host genes may be readily assessed. The greater abundance of such target molecules indicative of expression of host response genes not only allows such assessments to be made at an earlier time, but may also improve the accuracy of the assessment.

Further, the methods of the invention, which involve assaying a sample representative of gene expression to obtain data indicative of the relative abundance of target molecules indicative of the expression of genes associated with the subject's host response to bacterial infections may be useful in determining the presence of a non-bacterial infection. This is due to the ability to rule out a bacterial infection based on the relative gene expression data. As mentioned above, ruling out a bacterial infection is advantageous as it prevents the subject from receiving unnecessary antibiotic treatment, reduces healthcare costs, and reduces risk of developing antibiotic resistance.

As mentioned above, an infection may be a combined bacterial and non-bacterial infection. The inventors believe that the methods of first and second aspects of the invention may also be useful in detecting the presence of a bacterial infection in such a combined infection.

Detecting Lower Respiratory System Infections

The methods of the invention are methods are particularly suitable for use in detecting a lower respiratory system infection in a subject, whether it be a bacterial or non-bacterial infection.

Once a lower respiratory system infection has been detected by a method of the invention an additional step may optionally be practiced, to confirm the detection. The additional step may comprise performing a further diagnostic test for a lower respiratory system infection. Such a further diagnostic test may be used to identify the bacterial pathogen present, if the infection is determined to be bacterial, or to provide information regarding the susceptibility of the bacterial pathogen to antimicrobial agents. Bacterial culture is an example of a test which may be used to identify the bacterial pathogen and/or its susceptibility to antimicrobial agents.

Examples of other such diagnostic tests that may be employed will be well known to those skilled in the art. Suitably the further diagnostic test may comprise a chest x-ray. Bacteria collected as part of the further diagnostic test may be investigated by culturing.

Monitoring the Therapeutic Effectiveness of a Treatment

The tenth aspect of the present invention allows the monitoring of the effectiveness of a treatment for an infection.

Advantageously, the present inventors have discovered that the methods of detecting an infection of the invention still function to a high level of accuracy and specificity after a subject has begun receiving treatment for an infection. Therefore, the data indicative of the relative abundance of target molecules indicative of the expression of one or more gene pairs associated with the subject's host response can be measured before treatment and during treatment and after treatment.

Suitably, data indicative of the relative abundance of target molecules indicative of the expression of one or more gene pairs associated with the subject's host response can be used to monitor the progression of an infection during treatment, and thereby the effectiveness of said treatment.

Suitably the data indicative of the relative abundance of target molecules indicative of the expression of one or more gene pairs from the first sample and second sample is analysed.

Suitably the data indicative of the relative abundance of target molecules indicative of the expression of one or more gene pairs from the first sample and second sample is analysed to calculate the relative abundance ratio of the one or more gene pair(s) in the first sample and second sample as explained elsewhere herein.

Suitably comparing the data indicative of the relative abundance of the target molecules in the first sample and second sample comprises comparing the relative abundance ratio of the one or more gene pair(s) in the first sample and second sample.

Suitably therefore a difference in the relative abundance of target molecules indicative of the expression of at least one gene pair between the first sample and second sample comprises a difference in the relative abundance ratio of the one or more gene pair(s) between the first sample and second sample.

Suitably, a difference in the relative abundance ratio of the one or more gene pair(s) between the first sample and second sample indicates a change in respect of the progress of the infection.

Suitably, the change in respect of the progress of the infection may be caused by the infection itself or may be in response to treatment. Suitably the change in respect of the progress of the infection may be an improvement or a worsening in the infection.

In one embodiment, when monitoring a bacterial infection, an increase in the relative abundance of target molecules indicative of the expression of at least one gene pair between the first sample and second sample indicates a worsening in respect of the infection. In such an embodiment, an increase in the relative abundance of the target molecules indicative of the expression of at least one gene pair between the first sample and second sample indicates the treatment is ineffective. Suitably, in such an embodiment, an increase in the relative abundance ratio of the one or more gene pair(s) between the first sample and the second sample indicates a worsening in respect of the infection, and suitably indicates that the treatment is ineffective.

Accordingly, in such an embodiment when monitoring a bacterial infection, a decrease in the relative abundance of the target molecules indicative of the expression of at least one gene pair between the first sample and second sample indicates an improvement in respect of the infection. In such an embodiment, a decrease in the relative abundance of the target molecules indicative of the expression of at least one gene pair between the first sample and second sample indicates the treatment is effective. Suitably, in such an embodiment, a decrease in the relative abundance ratio of the one or more gene pair(s) between the first sample and the second sample indicates an improvement in respect of the infection, and suitably indicates that the treatment is effective.

Suitable measurement of the relative abundance of the target molecules indicative of the expression of at least one gene pair associated with the subject's host response is described elsewhere herein.

Suitably, the first sample is taken at a first timepoint and the second sample is taken at a second timepoint. Suitably the second time point is after treatment is provided to the subject.

Suitable treatments for bacterial and non-bacterial infections are described elsewhere herein. Suitably the relevant bacterial or non-bacterial treatment is provided to the subject in accordance with the infection that has been diagnosed.

Suitably the second sample is taken up to 1 hour, 2 hours, 3 hours, 4 hours, 5 hours, 7 hours, 10 hours, 12 hours, 15 hours, 20 hours, 24 hours, 48 hours, or 72 hours, after treatment is provided to the subject.

Suitably, the monitoring methods of the invention may make use of further samples at further timepoints (for example a third sample at a third timepoint, in addition to the first and second samples).

The first, second (and any subsequent) timepoints may be separated by any time period during which it is wished to monitor the therapeutic effectiveness of a treatment.

Suitably the time period may be hours, days, or weeks. Suitably the time period may be up to 1 hour, 2 hours, 3 hours, 4 hours, 5 hours, 7 hours, 10 hours, 12 hours, 15 hours, 20 hours, 24 hours, 48 hours, 72 hours, etc.

A subject

The methods and medical uses are practiced in respect of a subject. The subject may be one requiring diagnosis or treatment for an infection, such as a bacterial or non-bacterial infection. In one embodiment, the subject is one requiring diagnosis or treatment for a lower respiratory tract infection or a bacterial infection syndrome.

Suitably the subject may be a human subject. The subject may be a patient undergoing medical care, or an individual requesting medical care.

In the methods of the first, second, fourth, fifth, eighth, ninth and tenth aspect of the invention, a suitable subject may be one believed to have a bacterial infection, such as a bacterial lower respiratory system infection or a bacterial infection syndrome. For example, a suitable subject may have symptoms consistent with a lower respiratory system infection bacterial infection, such as shortness of breath, weakness, fever and/or a cough. In such cases the methods of the invention may be of use in definitively detecting or diagnosing a bacterial infection to warrant treatment with an antibiotic agent. Alternatively, a suitable subject may lack some or all symptoms consistent with a lower respiratory system infection. As considered elsewhere in this specification, such a subject may be substantially asymptomatic.

Alternatively, a suitable subject in the context of the methods of the present invention may be one believed to be at risk of developing an infection, or suffering from an infection, such as a bacterial or non-bacterial lower respiratory system infection. Such a subject may have been in contact with an individual suffering from a bacterial infection or non-bacterial infection, or may suffer from another disorder, which may render the subject at risk of developing a bacterial or non-bacterial infection.

Alternatively still, in the method of the tenth aspect of the invention, a suitable subject may be one already diagnosed with an infection, such as a bacterial or non-bacterial infection. In such cases the methods of the invention may be of use in monitoring the effectiveness of a treatment provided to the subject.

Suitably the subject is human. Suitably the subject is male or female. Suitably the subject is an adult or a child.

A Sample Representative of Gene Expression in a Subject

The methods of the invention make use of samples that are representative of gene expression in the subject in respect of whom the method is being practiced. In particular, the methods of the invention use samples representative of expression of host response genes involved in a subject's response to bacterial infection. Methods of the invention may make use of any sample which contains target molecules that provide a representation of such gene expression in the subject in question.

In suitable embodiment, the sample is a body fluid sample. Alternatively, suitable samples may include tissue samples, such as biopsies. In either case, a suitable sample (whether of a body fluid or tissue) may comprise biological cells from the subject that are involved in the host response to bacterial infection.

A suitable body fluid sample may include: a blood sample (for example, a whole blood sample, a blood plasma sample, or a serum sample); or a cerebrospinal fluid (CSF) sample, or a synovial fluid sample.

Blood samples are particularly suitable for use in the methods of the invention. The use of a blood sample (typically whole blood) is advantageous, since it is readily accessible. Additionally obtaining the sample is not associated with much less risk and patient discomfort than is the case for samples such as CSF, which is particularly advantageous in subjects with a suspected meningitis infection.

Samples may be processed for the enrichment of target molecules. Suitable techniques for such enrichment may be determined with reference to the nature of the sample, and of the target molecule in question. Generally, examples of suitable techniques (such as techniques for the isolation of biological cells from a sample, and the preparation of the cells to yield gene transcripts) will be well known to those skilled in the art.

Target Molecules

Target molecules suitable for use in the method of the invention are any molecules which are representative of gene expression in the subject. Such target molecules may be representative of gene expression either directly or indirectly. By way of example, a suitable target molecule which is directly representative of gene expression may comprise an RNA transcript. A suitable target molecule which is indirectly representative of gene expression may comprise a protein encoded by the gene.

It will be appreciated that the selection of the type of target molecule to be used in a method of the invention should be considered in connection with the nature of the sample representative of gene expression. In the case of a sample that contains host cells, a suitable target molecule may be either directly indicative of gene expression (such as an RNA transcript), or indirectly indicative of gene expression (such as a protein encoded by an expressed gene). In the case of a sample that is essentially acellular, the use of target molecules that are indirectly indicative of gene expression may be preferred, since such target molecules (an in particular protein examples of such target molecules) may be shed into the sample, even in the absence of biological cells.

By the same token, the nature of the target molecule, and therefore the nature of the sample representative of gene expression, may be chosen in order to be consistent with use in a preferred assaying system.

Assaying

When practicing the methods of the invention, the sample is assayed to determine the relative abundance of the target molecules indicative of the gene expression of interest. Generally, techniques suitable for assaying gene expression in order to provide information regarding relative abundance will be known to the person skilled in the art. As set out above, a suitable assay technique may be chosen with reference to the nature of the sample and the target molecules.

Merely by way of example, gene expression can be measured directly by techniques that allow the detection and quantification of RNA target molecules, such as RT-PCR, real-time PCR, Northern blot, RNA sequencing (RNA-seq) and RNA microarray.

Gene expression can be measured indirectly, by techniques that allow the detection and quantification of protein target molecules, such as ELISA, radioimmunoassay, immunoprecipitation, Western blot and mass spectrometry. Other suitable techniques for assaying proteins may be known to the person skilled in the art.

Suitably, gene expression of multiple genes or multiple pairs of genes, as is of interest in the present invention, may be measured simultaneously for example by a combinatorial assay. For example, the methods of the invention may be conducted by multiplex PCR. Alternatively, the methods of the invention may be conducted by multiple PCR tests.

Advantageously, each of the genes/gene pairs for use in the methods of the invention are suitable for detection by PCR.

Data Indicative of Relative Abundance of Target Molecules

The methods of the invention involve obtaining data indicative of the relative abundance of relevant target molecules indicative of gene expression. For the purposes of the present invention, such "data indicative of relative abundance" may be taken as encompassing any data that are capable of being used in determining the presence of an infection, such as a bacterial or non-bacterial infection, in a subject. In a suitable embodiment the data provide a quantitative indication of relative abundance of expression of members of gene pairs, for example with reference to relevant target molecules.

To determine whether an infection, such as a bacterial or non-bacterial infection is present, the data indicative of relative abundance of target molecules may be analysed as further shown in the Examples section of this specification.

Genes and gene pairs suitable for use in the methods of the invention

The methods of the invention involve obtaining data indicative of the relative abundance of target molecules indicative of the expression of at least the gene pair DUSP1 and IFI27. These genes are first and second host response genes, respectively.

The genes referred to herein are identified as follows:

TABLE 1

| Gene | Encodes |
| --- | --- |
| ELANE | neutrophil elastase |
| IFI44L | Interferon-induced protein 44-like |
| CTSG | Cathepsin G |
| S1PR5 | sphingosine-1-phosphate receptor 5 |
| GRK6 | G protein-coupled receptor kinase 6 |
| TXLNA | taxilin alpha |
| DUSP1 | dual specificity phosphatase 1 |
| APMAP (formerly C20orf3) | adipocyte plasma membrane associated protein |
| KMT2A | lysine (K)-specific methyltransferase 2A |
| HP1BP3 | heterochromatin protein 1, binding protein 3 |
| SIGLEC1 | sialic acid binding Ig-like lectin 1, sialoadhesin |
| IFI27 | interferon, alpha-inducible protein 27 |
| NMT1 | N-myristoyltransferase 1 |
| FLOT1 | flotillin 1 |
| HUWE1 | HECT, UBA and WWE domain containing 1, E3 ubiquitin protein ligase |

In a suitable embodiment, the methods of the invention involve obtaining data indicative of the relative abundance of target molecules indicative of the expression of the gene pair DUSP1 and IFI27 and optionally a further gene pair.

Suitably, the further gene pair may be selected from any of the gene pairs set out in Table 2.

TABLE 2

| First gene | Second gene |
| --- | --- |
| DUSP1 | SIGLEC1 |
| ELANE | IFI27 |
| DUSP1 | IFI44L |
| ELANE | SIGLEC1 |
| ELANE | IFI44L |
| CTSG | IFI44L |
| ELANE | S1PR5 |
| CTSG | S1PR5 |
| GRK6 | TXLNA |
| APMAP | KMT2A |
| DUSP1 | HP1BP3 |
| FLOT1 | NMT1 |
| APMAP | HUWE1 |
| ELANE | SIGLEC1 |
| DUSP1 | NMT1 |

More suitably, the further gene pair may be selected from the gene pairs set out in Table 3.

TABLE 3

| First gene | Second gene |
| --- | --- |
| DUSP1 | SIGLEC1 |
| ELANE | IFI27 |
| DUSP1 | IFI44L |
| ELANE | SIGLEC1 |
| ELANE | IF144L |

In a suitable embodiment methods of the invention may involve obtaining data indicative of the relative abundance of target molecules indicative of the expression of any one of the further gene pairs set out in Table 2, in addition to the gene pair DUSP1 and IFI27.

In a suitable embodiment methods of the invention may involve obtaining data indicative of the relative abundance of target molecules indicative of the expression of at least one, at least two, at least three, at least four, at least five, at least six, at least seven, at least eight, at least nine, at least ten, at least eleven, at least twelve, at least thirteen, at least fourteen, or all further gene pairs set out in Table 2, in addition to the gene pair DUSP1 and IFI27.

In a suitable embodiment methods of the invention may involve obtaining data indicative of the relative abundance of target molecules indicative of the expression of any one of the further gene pairs set out in Table 3, in addition to the gene pair DUSP1 and IFI27.

In a suitable embodiment methods of the invention may involve obtaining data indicative of the relative abundance of target molecules indicative of the expression of at least one, at least two, at least three, at least four, or all further gene pairs set out in Table 3, in addition to the gene pair DUSP1 and IFI27.

Suitably, in an embodiment where data indicative of the relative abundance of target molecules indicative of the expression of one further gene pair is obtained, the further gene pair is ELANE and IFI27.

Suitably, in an embodiment where data indicative of the relative abundance of target molecules indicative of the expression of two further gene pairs is obtained, the further gene pairs are firstly ELANE and IFI27, and secondly DUSP1/SIGLEC1.

Suitably, the methods of the invention may involve obtaining data indicative of the relative abundance of target molecules indicative of the expression of additional gene pairs beyond those set out in tables 2 or 3.

The expression of the genes and gene pairs is investigated by assaying the sample for target molecules indicative of the expression of such host response genes, as referred to above.

Determining the Presence of an Infection

Suitably, in the methods of the invention, the step of determining comprises using the data indicative of the relative abundance of target molecules indicative of the expression of the one or more gene pair(s) to perform discriminant analysis.

Suitably, discriminant analysis or discriminant function analysis is a method used to find a combination of features (for example expression levels for a combination of host response genes) that separates two classes (for example bacterial infections from non-bacterial infections). Suitably the combination of features may be the expression levels of one or more gene pair(s) under consideration. Suitably, the expression levels of the one or more gene pair(s) under consideration are determined from the data indicative of the relative abundance of target molecules indicative of the expression of the host response genes in each of the one or more gene pair(s).

Consequently, the presence of a bacterial infection in the subject is determined to be present if the relative abundance of target molecules indicative of the expression of the one or more gene pair(s) under analysis satisfies a predetermined condition. By the same token, in a subject where the relative abundance of target molecules indicative of the expression of the one or more gene pair(s) under analysis don't satisfy the predetermined condition, the presence of a non-bacterial infection is determined.

Suitable combinations of features i.e. gene pairs that may be employed in the methods of the invention are described herein, as are the means to determine the expression levels of one or more genes in each gene pair using the relative abundance of target molecules.

Suitably the predetermined condition is satisfied if the calculated result of the discriminant analysis exceeds a predetermined threshold. An example of a suitable predetermined threshold that may be employed with reference to a discriminant analysis is described in the examples section.

Suitably, the result of the discriminant function analysis provides the resulting relative abundance calculation which is suitable for use with the combination of gene pair(s) under consideration.

Suitably the relative abundance calculation provides the relative abundance ratio of the one or more gene pair(s) under analysis.

Suitably, the relative abundance ratio of the one or more gene pair(s) is compared to a predetermined threshold.

In one embodiment, the step of determining comprises calculating the relative abundance ratio of the one or more gene pair(s) under consideration.

Suitably, the relative abundance ratio of the one or more gene pair(s) is a ratio of the abundance of the first listed gene(s) relative to the abundance of the second listed gene(s) in the or each gene pair.

Suitably, the presence of a bacterial infection in the subject is determined to be present if the abundance of the first listed gene(s) is increased relative to the abundance of the second listed gene(s).

Suitably, the presence of a non-bacterial infection in the subject is determined to be present if the abundance of the second listed gene(s) is increased relative to the abundance of the first listed gene(s).

In one embodiment, an increase in the abundance of DUSP1 relative to the abundance of IFI27 in a sample indicates the presence of a bacterial infection in a subject.

In one embodiment, an increase in the abundance of IFI27 relative to the abundance of DUSP1 in a sample indicates the presence of a non-bacterial infection in a subject.

In one embodiment, the step of determining comprises calculating the relative abundance ratio of the one or more gene pair(s) under consideration using a relative abundance calculation. Suitably the relative abundance calculation is determined using discriminant analysis as explained above. Suitably the relative abundance calculation is a linear equation.

In one embodiment, the relative abundance ratio is calculated from a relative abundance calculation such as:

$$D=(1.03*\log(1/\text{Gene }A+\text{Gene }B)/(1/\text{Gene }C+\text{Gene }D))$$

In such an embodiment, the step of determining further comprises assessing whether the result of the relative abundance calculation is above a predetermined threshold. Suitably, the result of the calculation is the relative abundance ratio (D).

Suitably, the presence of a bacterial infection in the subject is determined to be present if the result of the discriminant function satisfies a predetermined condition. Suitably, therefore, the presence of a bacterial infection in the subject is determined to be present if the relative abundance ratio satisfies a predetermined condition.

Suitably, the presence of a non-bacterial infection in the subject is determined to be present if the result of the discriminant function does not satisfy a predetermined condition. Suitably, therefore, the presence of a non-bacterial infection in the subject is determined to be present the relative abundance ratio does not satisfy a predetermined condition.

In one embodiment, the determining step comprises comparing the relative abundance ratio of the one or more gene pair(s) under consideration to a predetermined threshold value.

In one embodiment, the determining step comprises determining whether the relative abundance ratio of the one or more gene pair(s) under consideration exceeds a predetermined threshold.

Suitably the predetermined threshold is a relative abundance ratio of at least 1.18. Suitably, therefore the predetermined threshold is D>1.18.

In one embodiment, the determining step comprises determining whether the relative abundance ratio of the one or more gene pair(s) under consideration exceeds 1.18.

Suitably, the presence of a bacterial infection in the subject is determined to be present if the relative abundance ratio of the one or more gene pair(s) under consideration satisfies the predetermined condition. Suitably, the presence of a bacterial infection in the subject is determined to be present if one or more of the gene pair(s) under consideration has a relative abundance ratio of greater than 1.18.

Suitably, the presence of a non-bacterial infection in the subject is determined to be present if relative abundance ratio of the one or more of gene pair(s) under consideration has a relative abundance ratio which does not satisfy a predetermined condition. Suitably, the presence of a non-bacterial infection in the subject is determined to be present if one or more of the gene pairs under consideration has a relative abundance ratio of less than 1.18.

Suitably, the methods of the invention are able to determine the presence of an infection, and are able to distinguish between bacterial and non-bacterial infections, with at least 70%, at least 80%, at least 90%, at least 95% or 100% sensitivity.

Suitably, the methods of the invention are able to determine the presence of an infection, and are able to distinguish between bacterial and non-bacterial infections, with at least 70%, at least 80%, at least 90%, at least 95% or 100% specificity.

Suitably, the methods of the invention are able to determine the presence of an infection, and are able to distinguish between bacterial and non-bacterial infections, with at least 70%, at least 80%, at least 90%, at least 95% or 100% accuracy.

In one embodiment, the methods of the invention are able to determine the presence of an infection, and are able to distinguish between bacterial and non-bacterial infections, with 100% sensitivity, 100% specificity and 100% accuracy.

The examples provided herein advantageously demonstrate that testing for the relative abundance of transcripts of the gene pair DUSP1 and IFI27, provides 100% sensitivity, accuracy and specificity in determining the cause of an infection in patients. This level of sensitivity, accuracy and specificity is maintained when combined with testing for the relative abundance of transcripts of other gene pairs.

Treatment of Infection

The eighth aspect of the invention relates to a method of treating an infection in a subject, the method comprising:
  (a) assaying a sample representative of gene expression in the subject to obtain data indicative of the relative abundance of target molecules indicative of the expression of at least the gene pair DUSP1 and IFI27;
  (b) determining the presence of an infection in the subject in dependence on the data;

(c) providing treatment for an infection when the determination indicates the presence of an infection.

In a suitable embodiment, the infection may be a bacterial infection or a non-bacterial infection. This embodiment gives rise to additional aspects of the invention.

In one aspect, the invention relates to a method of treating a bacterial infection in a subject, the method comprising:
- (a) assaying a sample representative of gene expression in the subject to obtain data indicative of the relative abundance of target molecules indicative of the expression of at least the gene pair DUSP1 and IFI27;
- (b) determining the presence of a bacterial infection in the subject in dependence on the data;
- (c) providing treatment for a bacterial infection when the determination indicates the presence of a bacterial infection.

In another aspect, the invention relates to a method of treating a non-bacterial infection in a subject, the method comprising:
- (a) assaying a sample representative of gene expression in the subject to obtain data indicative of the relative abundance of target molecules indicative of the expression of at least the gene pair DUSP1 and IFI27;
- (b) determining the presence of a non-bacterial infection in the subject in dependence on the data;
- (c) providing treatment for a non-bacterial infection when the determination indicates the presence of a non-bacterial infection.

In the context of the present disclosure, treatment of bacterial infections, such as bacterial lower respiratory system infections or bacterial meningitis, will generally involve the provision of antibacterial agents to a subject requiring such treatment. Suitable antibacterial agents include antibiotics such as those selected from the group consisting of: third generation cephalosporins (e.g. ceftriaxone, cefotaxime), ampicillin, penicillin G, meropenem, fluoroquinolone, trimethoprim-sulfamethoxazole, and chloamphenicol.

Suitably an antibacterial agent for use in accordance with this aspect of the invention may be selected with reference to the nature of the bacteria giving rise to the bacterial infection, such as bacterial meningitis, to be treated.

Thus, in the case of a bacterial infection with *Streptococcus pneumoniae* an antibacterial agent for use in accordance with this aspect of the invention may be selected from the group of: vancomycin plus a third-generation cephalosporin; ceftriaxone or cefotaxime; Meropenem (C-III), fluoroquinolonec (B-II).

Thus, in the case of a bacterial infection with *Neisseria meningitidis* an antibacterial agent for use in accordance with this aspect of the invention may be selected from the group of: a third-generation cephalosporin; Ceftriaxone; Penicillin G, ampicillin, chloramphenicol, fluoroquinolone, aztreonam.

Thus, in the case of a bacterial infection with *Listeria monocytogenes* an antibacterial agent for use in accordance with this aspect of the invention may be selected from the group of: Ampicillin (optionally with addition of an aminoglycoside) or penicillin G (optionally with addition of an aminoglycoside) Trimethoprim-sulfamethoxazole, meropenem (B-III).

Thus, in the case of a bacterial infection with *Streptococcus agalactiae* an antibacterial agent for use in accordance with this aspect of the invention may be selected from the group of: Ampicillind or penicillin G (optionally with addition of an aminoglycoside) Third-generation cephalosporins (B-III).

Thus, in the case of a bacterial infection with *Haemophilus influenzae* an antibacterial agent for use in accordance with this aspect of the invention may be selected from the group of: Third-generation cephalosporin, Ceftriaxone; (A-I) Chloramphenicol, cefepime (A-I), meropenem (A-I), fluoroquinolone.

Thus, in the case of a bacterial infection with *Escherichia coli* an antibacterial agent for use in accordance with this aspect of the invention may be selected from the group of: Third-generation cephalosporin, ceftriaxone, (A-II) Cefepime, meropenem, aztreonam, fluoroquinolone, trimethoprim-sulfamethoxazole.

Other suitable antibacterial agents will be known to those skilled in the art.

In the context of the present disclosure, treatment of non-bacterial infections may involve treatment with an anti-viral, an anti-parasitic, an anti-protozoan, or an anti-fungal agent as appropriate to the infection.

Merely by way of example, an anti-viral agent may be selected from the group consisting of an adamantane anti-viral agent, a chemokine receptor antagonist, an anti-viral interferon, an integrase strand transfer inhibitor, a neuraminidase inhibitor, a non-nucleoside reverse transcriptase inhibitor, a non-structural protein 5A (NS5A) inhibitor, a nucleoside reverse transcriptase inhibitor, a protease inhibitor and purine nucleoside. Other suitable anti-viral agents will be known to those skilled in the art.

Merely by way of example, an anti-parasitic agent may be selected from the group consisting of Artemether, Albendazole, Amphotericin B, Eflornithine, Furazolidone, Ivermectin, Mebendazole, Melarsoprol, Metronidazole, Nifursemizone, Nitazoxanide, Ornidazole, Paromomycin sulphate, Pentamidine, Praziquantal, Pyrimethamine, Quinapyramine, Rifampicin, Tinidazole Merely by way of example an anti-fungal agent may be selected from the group consisting of Abafungin, Albaconazole, Anidulafungin, Bifonazole, Butoconazole, Caspofungin, Clotrimazole, Econazole, Efinaconazole, Epoxiconazole, Fenticonazole, Fluconazole, Isoconazole, Ketoconazole, Luliconazole, Micafungin, Miconazole, Omoconazole, Oxiconazole, Sertaconazole, Sulconazole, Tioconazole, Isavuconazole, Itraconazole, Posaconazole, Propiconazole, Ravuconazole, Terconazole, Voriconazole.

The invention will now be further described with reference to the accompanying Experimental Results:

EXAMPLE 1

We have undertaken a preliminary study in suspected lower respiratory tract infection (LRTI) patients admitted to hospital in the UK (unpublished data). Adult patients (n=17) were identified to have confirmed bacterial (bacterial culture positive), confirmed viral (pathogen specific viral PCR positive) lower respiratory tract infection (with consistent chest X-ray changes).

Figure 1:
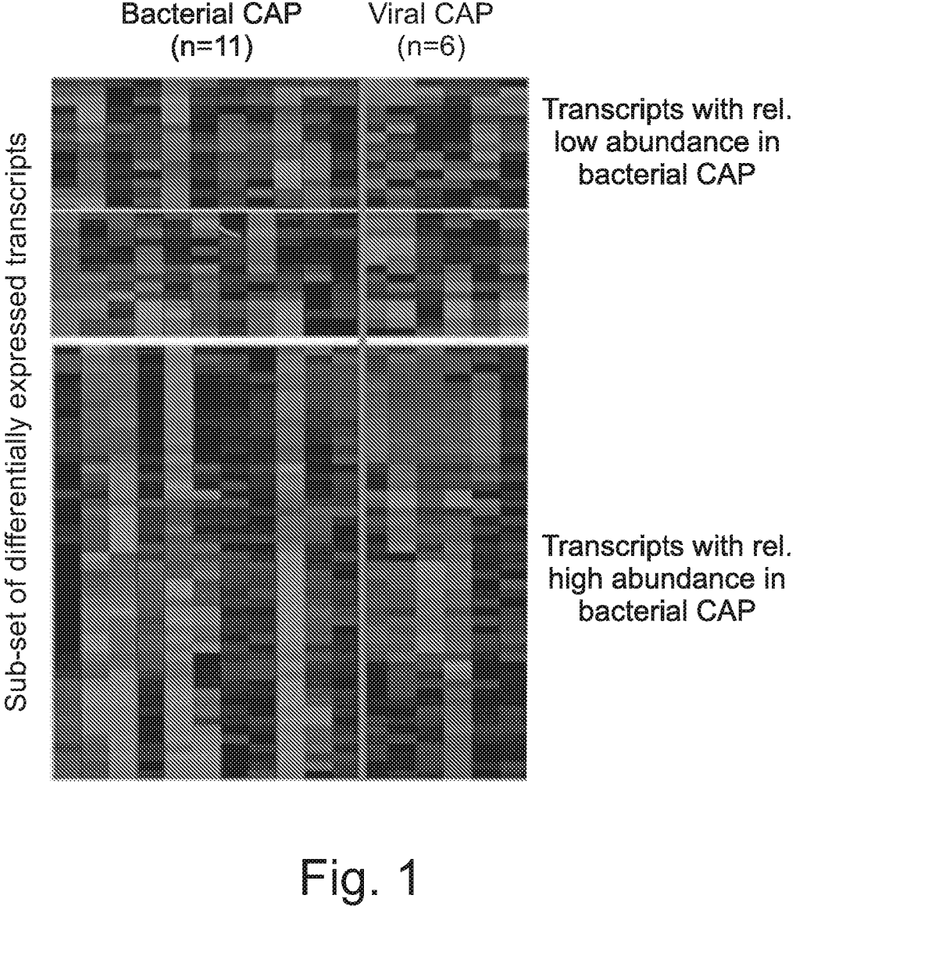
FIG. 1: Microarray data showing gene expression in community acquired pneumonia (CAP) patient samples from the UK via Agilent gene-expression micro-arrays (11 proven bacterial pneumonia, and six proven viral [influenza] pneumonia [bacteria proven by culture in blood and influenza proven by PCR on nasopharyngeal swab]). Based on relative transcript abundance dark areas–high abundance/light areas–low abundance) across the samples, 87 transcripts were significantly (false detection rate<5% [p<0.05]) differentially expressed among the group of proven bacterial CAP compared to others; a sub-set of transcripts exhibiting differential abundance are shown in FIG. 1. This data provided proof of principle that pairs of markers exhibiting reciprocal changes in expression between bacterial infections like bacterial CAP and viral infection mimics exist.

Microarray data: Venous whole blood samples of 2.5 ml were taken and collected in RNA stabilising tubes (PAXgene) during hospital admission before treatment had started. Total RNA was extracted using Blood RNA Extraction kits (PAXgene) following the manufacturer instructions. Total RNA (500 ng per sample) was amplified and labelled using Low Input Quick Amp. Labelling kits (Agilent). Patient sample derived amplified RNA was labelled with Cyanine-3. Control human amplified RNA (Universal RNA) was labelled with Cyanine-5. Labelled RNA (200 ng) was hybridised to SurePrint G3 GE 8×60K (Design ID 030495) human-specific microarrays following the manufacturers' instructions (Agilent Technologies). Arrays were scanned using Agilent G2505C scanner (Agilent Technologies). Raw fluorescent intensity was measured and initial quality control assessment undertaken using Agilent Feature Extraction software (FE 10.5.1.1). Transcripts exhibiting a statistically significant difference in relative transcript abundance between proven bacterial cases and proven non-bacterial cases were identified based on the fold change and false detection rate (FDR) output from SAM 4.0. (http://wwwstat.stanford.edu/~tibs/SAM). Gene-expression microarray analysis of the patients' blood samples confirmed multiple genes exhibited differential abundance in the host response to bacterial compared to non-bacterial (in this case viral) respiratory infections (FIG. 1).

Identifying top scoring pairs of markers: For our diagnostic, we aimed to identify pairs of markers (gene transcripts), where the first marker exhibited consistently higher expression than the 2nd marker in bacterial pneumonia cases. However in the comparator clinical group (viral infection), the expression ratio between the two markers changes, so that the 2nd marker, shows relatively consistent higher expression than the 1st marker. The "Top Scoring Pairs" of genes (TSPs) were identified using the open source program AUREA (Adapative Unified Relative Expression Analyser).

Validating marker gene pairs on a PCR platform: The most accurate TSPs based on the microarray data were re-tested using quantitative RT-PCR to confirm diagnostic accuracy on a measurement platform routinely available in hospital laboratories. One reason for assessing marker performance is that shorter sequences are interrogated (typically 20mer) using PCR compared to arrays (>60mer). This can affect marker performance. TSPs were tested using our original patient samples, so we could compare performance. Pairs were tested via proprietary TaqMan primer/probe sets (one probe set against each transcript). Probes were exon-spanning and biased towards the 3' end of mRNA. In pairs showing poor discrimination between groups, primers were re-designed based on array sequence. TSPs showing consistent performance by RT-PCR went forward.

Developing a logical equation based on multiple TSPs improves diagnostic specificity: Specificity of individual TSPs can be variable. However, specificity for multiple pairs of genes when combined via a Boolean operand can be used to create a diagnostic with high sensitivity and specificity. This approach was applied to the six TSPs (composed of 5 discriminatory genes) based on the RT-PCR data.

Figure 2:
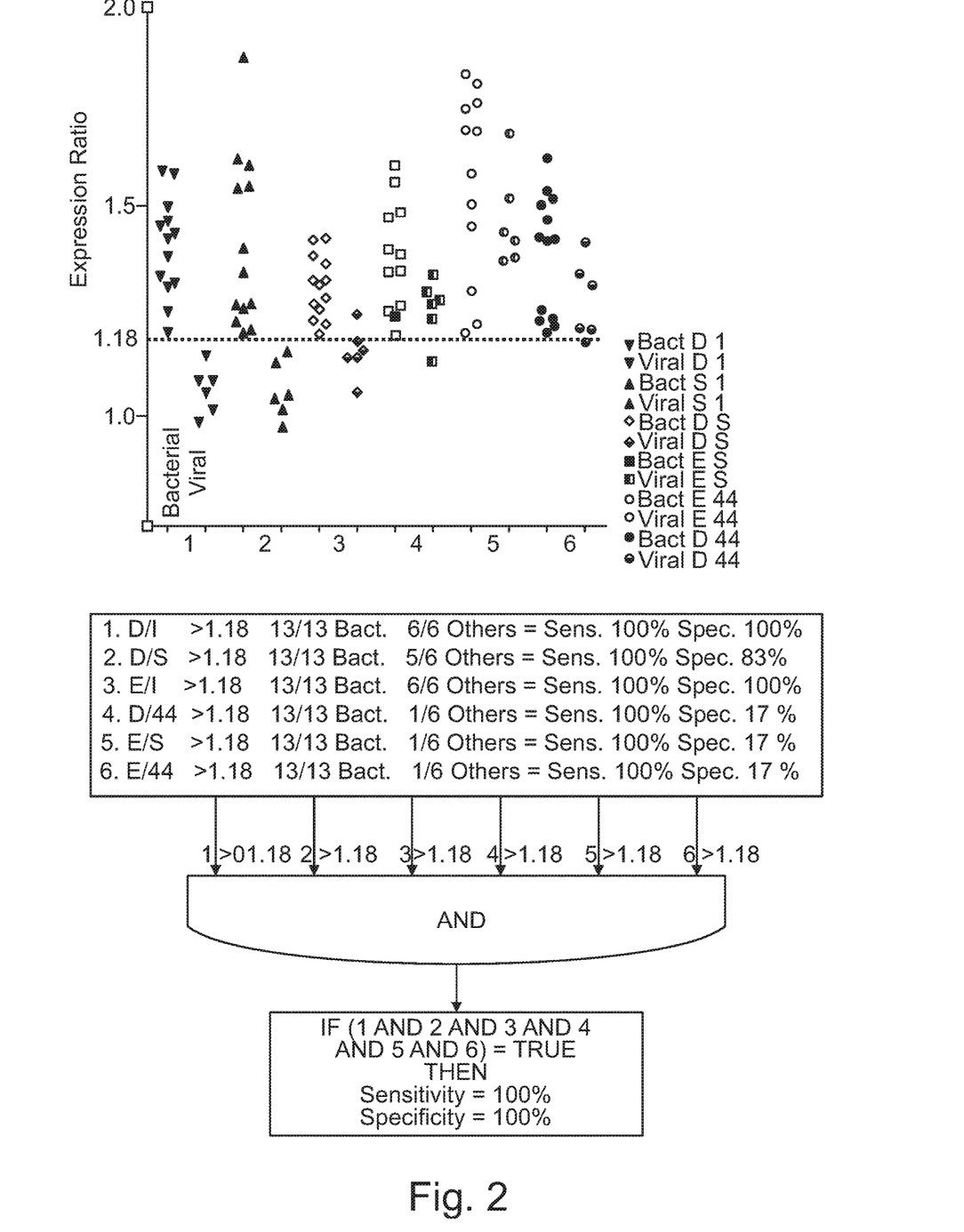
FIG. 2: A. Plot of expression ratio (Y-axis) for the six top scoring pairs of genes, from left to right: D/I-DUSP1/IFI27 [1]; E/I-ELANE/IFI27 [2]; D/S-DUSP1/SIGLEC1 [3]; E/S-ELANE/SIGLEC1 [4]; E/44-ELANE/IFI44L [5]; D/44-DUSP1/IFI44L [6]; measured via RT-PCR. Solid shapes represent bacterial pneumonia blood samples (n=13). Half-solid shapes represent viral respiratory [influenza] samples (n=6). The dotted horizontal line represents the predetermined threshold for the relative abundance expression ratio for classifying a sample as having a bacterial infection B. Sensitivity (sens.) and specificity (spec.) of each marker pair; C. Specificity for the pairs when combined via Boolean operand (AND). Using one to six gene pairs increases overall specificity from 17 to 89%.

Interpretation of marker abundance within a logical rule enabled sensitivity to be increased from 17% to 100% (Table 4, FIG. 2)

The resulting logical rule predicted a bacterial infection, if D>1.18, where D=1.49* (gene D/I) or alternatively D=1.67* (gene E/I) AND 1.49* (gene D/I) AND 1.035* (gene DIS) AND 1.68*(gene E144) AND 1.29*(gene D/44) AND 1.25*(gene E/S).

By way of further example, identification of the sample being as indicative of bacterial infection by relative transcript marker abundance ratio can also be arrived at using different equations. An example of such an alternative equation is as follows: if D [presence of bacterial infection] >1.1 where D=(1.03*log (1/Gene D)/(1/Gene I OR 1/Gene 44 OR 1/Gene S)).

The markers correctly distinguished bacterial LRTI (n=13) caused by a range of bacteria: *Streptococcus pneumoniae* (n=7); *Pseudomonas aeruginosa* (n=3); *Klebsiella pneumoniae* (n=1); *Legionella pneumonia* (n=1); *Escherichia coli* (n=1); *Haemophilus influenzae* (n=1) (note: 1 patient had infection involving 2 bacterial pathogens) from viral LRTI (n=6). Transcript marker pair specificity (with sensitivity set at 100%) in the respiratory sample set (samples with confirmed diagnosis n=19) are shown in Table 4 and FIG. 2.

TABLE 4

| Transcript marker pair | Sensitivity of detecting bacterial LRTI (n = 13) | Specificity (%) at classifying bacterial from viral LRTI (n = 6) | Accuracy (%) |
| --- | --- | --- | --- |
| DUSP1/IFI27 | 100% (13/13) | 100 (6/6) | 100 |
| DUSP1/SIGLEC1 | 100% (13/13) | 83 (5/6) | 95 |
| ELANE/IFI27 | 100% (13/13) | 100 (6/6) | 100 |
| DUSP1/IFI44L | 100% (13/13) | 17 (1/6) | 74 |
| ELANE/SIGLEC1 | 100% (13/13) | 17 (1/6) | 74 |
| ELANE/IFI44L | 100% (13/13) | 17 (1/6) | 74 |
| Combined | 100% (13/13) | 100 (6/6) | 100 |

EXAMPLE 2

Accuracy of the markers among different patient cohorts: There is critical need for improved diagnostic tests in both high and lower middle income countries. However, a host test may be complicated by patients being infected with different bacteria or a different host response (e.g. secondary to a different genetic background). To begin to assess our gene pair markers (E/44-ELANE/IFI44L; E/I-ELANE/IFI27; D/44-DUSP1/IFI44L; D/I-DUSP1/IF127; E/S-ELANE/SIGLEC1; D/S-DUSP1/SIGLEC1) in these circumstances we have examined marker performance using gene-expression data from other patient cohorts.

Blood samples were collected from adult patients in Australia on consecutive days, for 3-5 days of follow-up. Patients were confirmed to have severe bacterial pneumonia (n=6) or severe influenza A H1N1 (n=4). Looking at samples taken on day 1 of sampling only, 4 of the 5 transcript markers in combination were able to classify bacterial from viral infections with 100% sensitivity and 100% specificity (Table 5).

TABLE 5

| Transcript marker pair | Sensitivity of detecting bacterial LRTI (n = 6) | Specificity (%) at classifying bacterial from viral LRTI (n = 6) | Accuracy (%) |
| --- | --- | --- | --- |
| DUSP1/IFI27 | 100% (6/6) | 100 (4/4) | 100 |
| ELANE/IFI27 | 100% (6/6) | 100 (4/4) | 100 |
| DUSP1/IFI44L | 100% (6/6) | 100 (4/4) | 100 |
| ELANE/IFI44L | 100% (6/6) | 25 (1/4) | 70 |

Paediatric patients with bacterial infection syndromes were examined, focusing on pneumonia cases (n=12). The causative pathogens of pneumonia in this cohort included *Streptococcus pneumonia* (n=7) and *Staphylococcus aureus* (n=5). The data set also included viral influenza patients with fever (n=18). The 5 transcript markers distinguished bacterial pneumonia from viral infection with a sensitivity of 100% (12/12) and a specificity of 100% (18/18) as shown in table 6.

TABLE 6

| Transcript marker pair | Sensitivity of detecting bacterial LRTI (n = 12) | Specificity at classifying bacterial LRTI from viral infection (n = 18) | Accuracy (%) |
|---|---|---|---|
| DUSP1/IFI27 | 100% (12/12) | 100 (18/18) | 100 |
| DUSP1/SIGLEC1 | 100% (12/12) | 55 (10/18) | 91 |
| ELANE/IFI27 | 100% (12/12) | 100 (18/18) | 100 |
| DUSP1/IFI44L | 100% (12/12) | 67 (12/18) | 93 |
| ELANE/SIGLEC1 | 100% (12/12) | 78 (14/18) | 96 |
| ELANE/IFI44L | 100% (12/12) | 78 (14/18) | 96 |
| Combined | 100% (12/12) | 100 (18/18) | 100 |

Additional investigation of the diagnostic accuracy of the 5 transcript markers in other data-sets, demonstrated a high sensitivity and specificity in several patient cohorts distinguishing a range of different bacterial infections from viral infections.

Paediatric patients with a wider range of bacterial infection syndromes (n=58), including pneumonia, bacteraemia, urinary tract infection, pyelonephritis, abscess, meningitis and septic arthritis were examined. The causative pathogens for these infections included *Streptococcus pneumonia* (n=13), *Staphylococcus aureus* (n=16) and *Escherichia coli* (n=29). The transcript expression ratio for the different bacterial infection syndromes were again compared to influenza patients (n=18). The transcript markers distinguished bacterial from viral infection with a sensitivity of 100% (58/58) and a specificity of 89% (16/18), see Table 7.

TABLE 7

| Transcript marker pair | Sensitivity of detecting bacterial infection syndromes (bacteremia, urinary tract infection, pyelonephritis; n = 58) | Specificity (%) at classifying bacterial viral infection at sensitivity (n = 18 [influenza]) | Accuracy (%) |
|---|---|---|---|
| DUSP1/IFI27 | 100% (58/58) | 0 (0/18) | 77 |
| DUSP1/SIGLEC1 | 100% (58/58) | 50 (9/18) | 87 |
| ELANE/IFI27 | 100% (58/58) | 61(11/18) | 92 |
| DUSP1/IFI44L | 100% (58/58) | 28 (5/18) | 82 |
| ELANE/SIGLEC1 | 100% (58/58) | 50 (9/18) | 87 |
| ELANE/IFI44L | 100% (58/58) | 39 (7/18) | 85 |
| Combined | 100% (58/58) | 89 (16/18) | 98 |

Table 8 shows paediatric bacteraemia patients presenting to hospital with acute illness caused by Gram negative (*E. coli*) or Gram positive (*S. aureus* or *S. pneumonia*) bacteria present in the blood stream that were analysed. Diagnosis was established by bacterial blood culture. Adult or child viral patients (n=18) presenting to hospital with acute viral infection caused by influenza virus A were also analysed. Viral diagnosis was confirmed by direct fluorescent antigen or viral culture. The transcript markers distinguished bacteremia from viral infection with a sensitivity of 100% (20/20) and a specificity of 89% (16/18).

TABLE 8

| Transcript marker pair | Sensitivity of detecting bacteremia n = 20 | Specificity (%) at classifying bacteremia from viral infection (n = 18 [influenza]) | Accuracy (%) |
|---|---|---|---|
| DUSP1/IFI27 | 100% (20/20) | 39 (7/18) | 71 |
| DUSP1/SIGLEC1 | 100% (20/20) | 50 (9/18) | 76 |
| ELANE/IFI27 | 100% (20/20) | 61 (11/18) | 82 |
| DUSP1/IFI44L | 100% (20/20) | 28 (55/18) | 66 |
| ELANE/SIGLEC1 | 100% (20/20) | 50 (9/18) | 76 |
| ELANE/IFI44L | 100% (20/20) | 39 (7/18) | 71 |
| Combined | 100% (20/20) | 89 (16/18) | 95 |

Table 9 shows results from children presented to hospital with clinical features of meningococcal (bacterial) sepsis (n=24). *Neisseria meningitidis* was detected in blood (or CSF) by culture or PCR. Patient gene expression was compared against healthy adults (n=21). The transcript markers distinguished bacterial sepsis from health with a sensitivity of 100% (24/24, specificity of 71% (15/21) and an accuracy of 87% (39/45).

TABLE 9

| Transcript marker pair | Sensitivity (%) of detecting sepsis n = 24 | Specificity (%) at classifying sepsis from healthy controls (n = 21) | Accuracy (%) |
|---|---|---|---|
| DUSP1/IFI27 | 100% (24/24) | 5 (1/21) | 56 |
| DUSP1/SIGLEC1 | 100% (24/24) | 19 (4/21) | 62 |
| ELANE/IFI27 | 100% (24/24) | 5 (1/21) | 56 |
| DUSP1/IFI44L | 100% (24/24) | 0 (0/21) | 53 |
| ELANE/SIGLEC1 | 100% (24/24) | 62 (13/21) | 82 |
| ELANE/IFI44L | 100% (24/24) | 5 (1/21) | 56 |
| Combined | 100% (24/24) | 71 (15/21) | 87 |

Accuracy of the markers in patients with HIV co-infection: Given the host test is based on the body's response, the question arises as to whether the test will remain accurate among patients co-infected with HIV. This would be a particular concern in lower middle income countries (LMIC). To begin to address this, Malawian children presenting with invasive pneumococcal disease were examined. Half of the patients had HIV co-infection (n=6) and half did not (n=6), healthy patients (n=3) were also examined. The 5 transcript markers correctly distinguished all pneumococcal disease patients from healthy patients with a sensitivity of 100% (12/12) and specificity of 100% (3/3). This indicates the gene pairs can accurately identify bacterial infection syndromes among HIV+ positive patients.

Accuracy of the markers in distinguishing bacterial infection from parasitic infection: There is critical need for improved diagnostic tests in lower middle income countries. However, in this environment a host test may be complicated by patients being infected with parasites, such as malaria. To begin to assess six TSPs (E/44-ELANE/IFI44L; E/I-ELANE/IFI27; D/44-DUSP1/IFI44L; D/I-DUSP1/IFI27; E/S-ELANE/SIGLEC1; D/S-DUSP1/SIGLEC1) in these circumstances we have examined TSP performance using micro-array data from patients with proven bacterial infection and proven malaria.

Gene expression values from microarray analysis of RNA from blood of adult patients with *Plasmodium falciparum* malaria (both uncomplicated and severe cases with complications of impaired consciousness, acidosis and/or anemia) were compared with the gene expression levels in patients with bacterial meningitis for the following transcript markers: DUSP1, IF127 and IFI44L. In combination, these 3 transcript markers were able to classify cases of infections of bacterial meningitis from cases of *P. falciparum* malaria with a sensitivity of 100%, specificity of 93% and accuracy of 94% (Table 10)

TABLE 10

| Transcript marker pair | Sensitivity of detecting bacterial meningitis (n = 9) | Specificity (%) at classifying bacterial meningitis from malaria (n = 44) | Accuracy (%) |
| --- | --- | --- | --- |
| DUSP1/IFI27 | 100% (9/9) | 75 (33/44) | 80 |
| DUSP1/IFI44L | 100% (9/9) | 88 (39/44) | 91 |
| Combined | 100% (9/9) | 93 (41/44) | 94 |

EXAMPLE 3

Examining the impact of prior antibiotic exposure on test accuracy: Blood cultures are reported to be sterile within 2 and 4 hours of antibiotic exposure. Therefore pathogen directed diagnostics such as culture or PCR are less sensitive when patients have already received antibiotics (such as pre-hospital antibiotic treatment).

Figure 3:
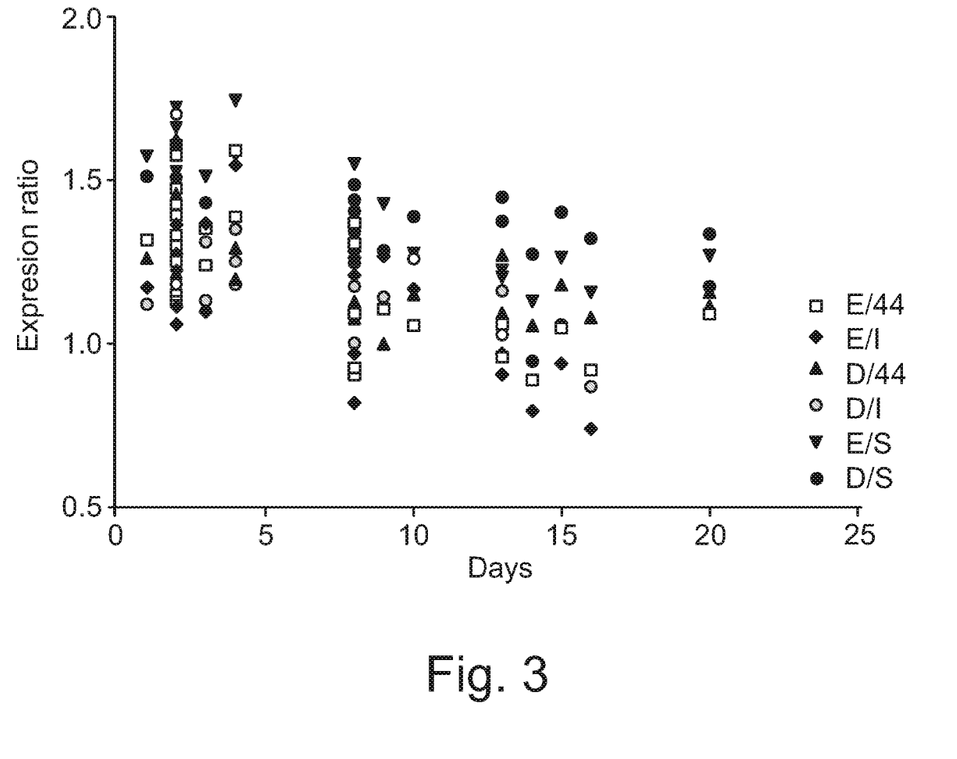
FIG. 3: Plot of expression ratio (Y-axis) for the six top scoring pairs of genes (E/44-ELANE/IFI44L; E/I-ELANE/IFI27; D/44-DUSP1/IFI44L; D/I-DUSP1/IFI27; E/S-ELANE/SIGLEC1; D/S-DUSP1/SIGLEC1) in bacterial infection samples (n=26). Each dot on the x-axis represents a sample. A different coloured/shaped dot on the y-axis corresponds to the same sample measured by a different gene pair. X-axis corresponds to the number of days the patient had been treated with antibiotics prior to sampling. There is a reduction in all gene pair expression abundance ratios among samples collected over 5 days after antibiotic initiation. Grouping patients by number of days on antibiotics (1-5, 6-10 and 11+ days) sensitivity was 1(13/13), 0.5 (3/6) and 0.28 (2/7) respectively.

To examine the impact of prior antibiotic exposure on the host genes, we assessed 6 transcript marker gene pairs (E/44-ELANE/IFI44L; E/I-ELANE/IFI27; D/44-DUSP1/IFI44L; D/I-DUSP1/IFI27; E/S-ELANE/SIGLEC1; D/S-DUSP1/SIGLEC1) in an extended set of bacterial (n=26) and mimic (n=150) patient samples. Tester was blinded to sample classification. The lower threshold of expression ratio for classifying a bacterial sample was set as −1.2 standard deviations below the mean expression ratio based on the bacterial samples previously measured. Unblinding, the test appeared to identify only 18/26 bacterial samples. However, on reviewing the clinical data, multiple bacterial samples were collected more than 5 days after initiation of intravenous antibiotics. There was a marked reduction in the transcript maker pairs expression ratio among patients exposed to over 5 days of antibiotics showing that the treatment was effective (FIG. 3).

Analysing bacterial samples collected within 5 days, the test exhibited 100% (13/13) sensitivity and 90% (135/150) specificity. Distinguishing between proven bacterial and viral infection the test exhibited 100% (13/13) sensitivity and 98% (51/52) specificity. This observation indicates the test can still accurately and sensitively detect bacterial infection up to 5 days after initiation of antibiotics. The observation also indicates that the test of the invention can be used to monitor treatment and help confirm the infection is resolving after treatment has been provided to a subject.

The invention claimed is:

1. A method of treating a symptomatic infection in a human subject, the method comprising:
   (a) assaying a body fluid sample obtained from the subject to determine the expression of at least the gene pair DUSP1 and IFI27 relative to each other;
   (b) determining the presence of a bacterial infection in the subject based on the presence of the expression of at least the gene pair DUSP1 and IFI27 relative to each other; and
   (c) treating the subject having the bacterial infection by administering a therapeutically effective amount of an antibacterial agent.

2. The method according to claim 1 wherein the infection is bacterial and is caused by a bacterium selected from the group consisting of: *Streptococcus pneumoniae; Staphylococcus aureus, Pseudomonas aeruginosa, Klebsiella pneumoniae; Legionella pneumonia, Escherichia coli*, and *Haemophilus influenza*.

3. The method according to claim 1 wherein the infection is a lower respiratory system infection caused by one or more pathogens selected from the group consisting of: *Streptococcus pneumoniae, Staphylococcus aureus, Streptococcus agalactiae, Streptococcus pyogenes, Pseudomonas aeruginosa, Bordatella pertussis, Neisseria meningitidis, Coxiella burnetiid, Corynebacterium, Klebsiella pneumoniae, Legionella pneumonia, Escherichia coli, Haemophilus influenza, Moraxella catarrhalis, Mycoplasma pneumoniae, Acinetobacter baumannii, Chlamydophila pneumoniae, Bordatella parapertussis, Neisseria gonorrhoeae, Campylobacter jejuni, Listeria monocytogenes, Chlamydophila psittaci, Coxiella burnetii, Francisella tularensis, Mycobacteria tuberculosis* and *nontuberculous mycobacteria*.

4. The method according to claim 3 wherein the lower respiratory system infection is pneumonia caused by one or more pathogens selected from the group consisting of: *Chlamydia pneumoniae, Escherichia coli, Haemophilus influenza, Klebsiella pneumoniae, Legionella pneumonia, Moraxella catarrhalis, Mycoplasma pneumoniae, Neisseria meningitidis, Pseudomonas aeruginosa, Staphylococcus aureus, Streptococcus agalactiae*, and *Streptococcus pneumoniae*.

5. The method according to claim 1 wherein the infection is a bacterial infection syndrome, selected from i) sepsis caused by a bacterium selected from the group consisting of: *Acinetobacter baumannii, Staphylococcus epidermidis, Staphylococcus saprophyticus, and Streptococcus pyogenes*, and ii) bacterial gastroenteritis.

6. The method according to claim 1 wherein the sample is selected from the group consisting of: a whole blood sample; a blood plasma sample; or a serum sample; a cerebrospinal fluid (CSF) sample; and a synovial fluid sample.

7. The method according to any preceding claim, wherein step (a) comprises determining the expression of at least one further gene pair relative to each other.

8. The method according to claim 7 wherein the at least one further gene pair is selected from the group: DUSP1 and SIGLEC1; ELANE and IFI27; DUSP1 and IFI44L; ELANE and SIGLEC1; ELANE and IFI44L; CTSG and IFI44L; ELANE and S1PR5; CTSG and S1PR5; GRK6 and TXLNA; APMAP and KMT2A; DUSP1 and HPIBP3; FLOTI and NMTI; APMAP and HUWE1; ELANE and SIGLEC1; and DUSP1 and NMTI.

9. The method according to claim 7 wherein the at least one further gene pair is selected from the group: DUSP1 and SIGLEC1; ELANE and IFI27; DUSP1 and IFI44L; ELANE and SIGLEC1; and ELANE and IFI44L.

10. The method according to claim 1 wherein step (b) comprises calculating the relative abundance ratio of the one or more gene pair(s).

11. The method according to claim 10 wherein step (b) comprises comparing the relative abundance ratio of the one or more gene pair(s) to a predetermined threshold value.

12. The method according to claim 11, wherein step (b) comprises determining whether the relative abundance ratio of the one or more gene pair(s) under consideration exceeds a predetermined threshold value, wherein the predetermined threshold value is 1.18.

13. A method of treating a symptomatic infection in a human subject, the method comprising:
   a. selecting a subject with a bacterial infection having an increased relative expression of the gene DUSP1 compared to the expression of the gene IFI27; or
   b. selecting a subject with a non-bacterial infection having an increased relative expression of the gene IFI27 compared to the expression of the gene DUSP1; and
   c. treating the subject with the bacterial infection with an effective amount of an antibacterial agent or the subject with the non-bacterial infection with an effective amount of an agent against a non-bacterial infection.

* * * * *